United States Patent [19]

Halpaap et al.

[11] 4,064,041

[45] Dec. 20, 1977

[54] SEPARATING MATERIAL FOR THIN LAYER CHROMATOGRAPHY

[75] Inventors: Herbert Halpaap; Walter Reich; Johannes Ripphahn, all of Darmstadt, Germany

[73] Assignee: Merck Patent Gesellschaft mit beschraenkter Haftung, Darmstadt, Germany

[21] Appl. No.: 690,728

[22] Filed: May 27, 1976

[30] Foreign Application Priority Data

May 30, 1975   Germany .............................. 2524065

[51] Int. Cl.² ............................................. B01D 15/08
[52] U.S. Cl. ................................ 210/31 C; 210/198 C
[58] Field of Search .......................... 210/31 C, 198 C; 55/386

[56] References Cited

U.S. PATENT DOCUMENTS

| | | | |
|---|---|---|---|
| 3,303,043 | 2/1967 | Halpaap et al. | 210/198 C |
| 3,502,217 | 3/1970 | Bruckner | 210/198 C |
| 3,782,075 | 1/1974 | Kirkland | 55/386 X |
| 3,922,431 | 11/1975 | Rapmacher | 210/198 C |

OTHER PUBLICATIONS

Chromatography by Heftmann, Reinhold Pub. Co., New York, N. Y. pp. 87-89, 1961.

Primary Examiner—John Adee
Attorney, Agent, or Firm—Miller & White

[57] ABSTRACT

A separating material for thin layer chromatography comprising an inert substrate coated with a sorption agent consisting essentially of silica gel particles about 3 to 8 $\mu$m in diameter in a layer 100–300 $\mu$m thick.

12 Claims, No Drawings

SEPARATING MATERIAL FOR THIN LAYER CHROMATOGRAPHY

BACKGROUND OF THE INVENTION

This invention relates to an improved silica gel sorption composition for use in this layer chromatography.

The increasing utilization of thin layer chromatography (TLC) has mandated the development of better separating materials, with greater value placed upon better efficiency with regard to effective separating ability and lowering the limits of detection as well as with regard to the reproducibility of results.

In thin layer chromatography there are usually employed carrier materials coated with sorption agents; silica gel layers on glass plates or on foils have found the greatest practical use. The particle sizes of these sorption agents, in the case of the best commercially available preparations, are on the order of about 5 to 25 $\mu m$ in diameter wherein the average particle sizes vary approximately between 10 and 15 $\mu m$. Smaller particle sizes have generally been regarded as disadvantageous since with decreasing particle size the flow rate of the elution agent decreases considerably so that the necessary separation times become too long; simultaneously, diffusion increases and separation ability is reduced. Therefore, even separation materials with coarse particles which are said to give a separation ability almost equal in value to the otherwise conventional TLC plates have been suggested, e.g., in Deutsche Apothekerzeitung, 113, page 791, 1973.

Chromatographic separations on ultra-thin silica gel and aluminum oxide layers have also been suggested, e.g., see Z. Chem. 1972, pages 152 and 153. As chromatographic material, there is used the undefined very fine grain portion which happens to remain adhering to the plate after rinsing of the carrier material. Therefore, reproducible and comparable results are not achievable with such layers. Furthermore, such ultra-thin layers are unsuitable for mechanical evaluation with the help of the most widely used remission measurements. The limitation to solely transmission measurements is a considerable disadvantage, as is the reduced suction force which permits only a horizontal development.

In order to avoid some of the above-indicated difficulties so-called thin film chromatography has been suggested, e.g., as described in German Pat. No. 1,943,304. Thin layers (<10 $\mu m$) applied by vapor deposition, for example indium oxide, are employed as the stationary phase. However, such vapor deposited layers exhibit an extremely small capillary action, from which result very flow rate coefficients, very slow running times and very low running heights of only a few mm. Therefore, only a very limited number of substances can be satisfactorily separated by this technique.

Thus, there still exists a need for efficient thin layer chromatography separating materials with which good separations can be carried out quickly and with good sensitivity. The present invention fills such a need.

OBJECTS OF THE INVENTION

Accordingly, it is a general object of this invention to provide an improved sorption composition for use in thin layer chromatography.

Another object of this invention is to provide TLC materials having improved separation effectiveness, sensitivity and reproducibility.

A further object of this invention is to provide improved TLC plates suitable for direct quantitative photometric determination of chromatographed substances in amounts below 10 ng.

Upon study of the specification and appended claims, further objects and advantages of this invention will become apparent to those skilled in the art.

SUMMARY OF THE INVENTION

Briefly, the above and other objects, features and advantages of the present invention are attained in one aspect thereof by providing a separating material for thin layer chromatography comprising a flat inert substrate having superimposed thereon a layer of sorption agent of substantially uniform thickness in the range of 100-300 $\mu m$ thick layer, said sorption agent consisting essentially of silica gel particles 3 to 8 $\mu m$ in diameter. (A "$\mu m$" is a micron, i.e., $1 \times 10^{-6}$ meter).

DETAILED DISCUSSION

It has now been found that highly efficient separating materials for thin layer chromatography can be prepared by coating conventional carrier materials with a silica gel of a definite and relatively small particle size with a very narrow particle size distribution in the layer thicknesses usual in TLC. The so-obtained separating materials are far superior in separating effectiveness to the best presently available thin layer chromatographic materials.

The present invention provides a separating material for thin layer chromatography comprising an inert substrate material coated with a thin layer of silica gel, wherein the silica gel layer can additionally contain binding agents and/or indicators, which is characterized in that the silica gel consists essentially of particles with a narrow particle size range between 3 and 8 $\mu m$, the silica gel layer thickness is about 100-300 $\mu m$ and the weight related specific surface area of the silica gel is about 0.5 to 0.7 $m^2/g$.

The present invention furthermore provides the use of a silica gel with a narrow particle size distribution between 3 and 8 $\mu m$, a weight related specific surface area between about 0.5 and 0.7 $mg^2/g$. and a thickness of 100 to 300 $\mu m$ on conventional carrier materials for the production of sorption agent layers suitable for thin layer chromatography. Conventional carriers are, for example, glass plates, aluminum foil, polyester film, etc.

In another aspect the present invention provides a process for the production of a separating material for thin layer chromatography by coating of a carrier material with silica gel which can contain binding agents and/or indicators, wherein an aqueous suspension of silica gel which consists essentially of particles with a narrow particle size range between 3 and 8 $\mu m$ is uniformly coated onto a substrate and dried to form a layer of 100 to 300 $\mu m$ in thickness.

Preferred layer thicknesses are in the range of between 125 and 250 $\mu m$. Separating materials with a layer thickness of below 100 or above 300 $\mu m$ but in all other aspects according to the present invention show in general a significant drop in their separation effectiveness.

Silica gels with a similar particle size spectrum are, in part, known as carrier materials in high pressure liquid chromatography; as is known, they are there employed with the use of high pressures (e.g., 20 to 200 atmospheres of pressure) in special apparatus involving a considerable technical expenditure. The high separation effectiveness in high pressure liquid chromatography depends precisely upon the combination of a carrier with a narrow particle size distribution packed into narrow columns of a few millimeters diameter and the use of high pressure to achieve high flow rates. The use of small particles can be compensated for by the use of high pressures up to a few hundred atmospheres. No satisfactory separations or no separations at all are achieved with small particle sizes under low or only hydrostatic pressures. (For a reference to this high pressure chromatography technique, see, e.g., the book of H. Engelhardt "Hochdruct-Fluessigkeits-Chromatographie," Springer-Verlag 1975).

An improvement in thin layer chromatography separation effectiveness by use of a silica gel with a relatively small particle size while maintaining layer thicknesses conventional in TLC could not be foreseen or expected because of the completely different flow properties in thin layer chromatography where no pressure is used at all but the solvent is transported only by capillary activity. According to the present invention, separating materials are now made available for TLC which provide decisively improved separation capacities without any additional expensive apparatus.

The most favorable particle size range for the separating materials according to the present invention lies at a more size of 3 to 8 $\mu$m. Contrary to previous conceptions, more effective thin layer plates can be produced with this finely divided material on layers of average strength (layer thickness 100 to 300 $\mu$m).

A very narrow particle size range is important for the quality of the separating materials according to this invention. Thus, at least 80 wt. %, preferably at least 85%, more preferably at least 90% of the silica gel particles are to possess a particle size between about 3 and 8 $\mu$m. In any case, a maximum of only about 10% of the total weight of silica gel particles is to lie either below 3 $\mu$m or above 8 $\mu$m. From the prior art, it could not be deduced that substantially better separating capacities could thereby be achieved than with the previously known materials employed in thin layer chromatography. Deviation from this particle size range, especially in the direction of smaller particles, leads to a clear drop of effectiveness.

The weight related specific surface area of the silica gel employed according to this invention is between about 0.5 and 0.7 m$^2$/g. Optimum separation results are achieved precisely within this narrow range. The corresponding values of the silica gels hitherto used in thin layer chromatography lie substantially lower, as a rule, e.g., below 0.3 m$^2$/g., while those of very finely ground silica gel lie substantially higher, e.g., at 1 m$^2$/g.

This solution according to the invention was surprising since, according to published results, e.g., Journal of Chromatography, 79, 1973, pages 179–185, and Naturwissenschaften, 60, 1973, page 553, one would have assumed that for improvement of separation effectiveness and for the achievement of an improved detection limit, not only the particle size but also the layer thickness of the silica gel would be lowered. Thus, e.g., a reduction of the layer thickness to 25 to 50 $\mu$m was required, which corresponds to about 1/10 to 1/20 of the otherwise usual TLC layer thicknesses of about 200 to 250 $\mu$m. Astonishingly, however, according to the present invention, outstanding separation effectiveness is achieved precisely when the conventional layer thicknesses are maintained while the conventional particle size is reduced. This was in no way to be foreseen from the experience of high pressure liquid chromatography since there, apart from the marked increase in the pressure, with reduction of the particle size there is also a reduction of the column cross-section. The number of particles in the cross-section of the layer should not be reduced in comparison with the previously usual TLC layers but better even be increased. In the case of dense packing, in the cross-section of the layers according to this invention, according to electron microscopic pictures, depending upon the layer thickness, about 20 to 60 particles are detectable.

The production of the separating materials takes place in the usual manner. As substrates, there can be employed all conventional materials; glass plates are generally preferred. However, foils can also be used, e.g. of aluminum, synthetic resin films, etc. The sorption agents are slurried in coatable aqueous suspensions and, after intensive mixing and optional degassing, applied to the substrate with conventional coating apparatus or coating devices. Usually, binding agents are added to the sorption agents to increase the adhesive strength and wear resistance, and/or indicators. The organic binding agents mentioned in German Pat. Nos. 1,443,446 or 1,517,929 are preferred. The most frequently employed indicator is a fluorescent indicator, preferably a manganese-activated zinc silicate which absorbs at 254 nm. in UV. The binding agents are, as a general rule, added in amounts of 0.1 to about 10%; the indicators in amounts of about 0.5 to 5 wt.%.

After coating, the separating materials are dried in the usual way. The coating devices are regulated so that the layer thicknesses obtained after drying lie between 100 and 300 $\mu$m. Drying usually takes place in drying canals at temperatures of about 120° to 150° C; the period of drying depends upon the length of the drying canal.

The separating materials obtained are, in their separation effectiveness, far superior to all conventional TLC preparations. Admittedly, especially in the case of comparatively long run lengths, the running time of the elution agent is somewhat longer. However, since shorter running lengths are employed because of the substantially improved separating capacity, this factor plays no part. The more than doubled number of theoretical plates more than offsets the reduced flow rate of elution agent, since the effectiveness of the separating material is principally assessed according to the number of theoretical plates available for a particular running height.

To illustrate the above, the separating materials of the present invention when employed in chromatography using a normal (N) chamber with chamber saturation, benzene as the elution agent at 22° C. and a running length of the elution agent of 20 to 30 mm., possess a speed coefficient K of 4 to 5 mm$^2$/sec. In the case of a running length of the elution agent of 40 to 80 mm., a speed coefficient $\kappa$ between 5 and 7 mm$^2$/sec. is typical.

Instead of conventional silica gel, there can also be used surface-modified silica gels, e.g., silanted silica gel or silica gel surface modified with organic radicals. Suitable silica gel types are commercially available and are described in the literature, e.g., see German application No. 2,357,184, K. Unger, Angewandte Chemie, Volume 84 (1972), page 331, German application No. 2,309,129 and German application No. 2,125,428.

The separating materials according to this invention are employed in the same way as conventional TLC finished preparations. They are especially suitable for the rapid detection of small amounts of substances detectable by TLC. Outstanding separations can be achieved even with volumes of 10 nl., corresponding to applied sample amounts of about 1 to 10 ng.; hitherto in micro-thin layer chromatography, substantially larger applied amounts were generally necessary.

Further, with the new separating material, for the first time quantitative photometric determinations of the chromatographed substances directly on the plate in the quantities below 10 ng. are possible e.g., with remission measurements. Substances with absorption in the visible or UV range can be detected with satisfactory standard deviations (maximum 10%) in quantities up to 200 pg. In measuring substances with inherent fluorescence, the same detection exactitude can be still achieved in the case of a tenfold lower quantity. Thus, e.g., in the case of the detection of aflatoxins with the help of a densitometer (excitation wavelength 366 nm., measurement wavelength 460 nm.), a correction curve was determined for the concentrations 200, 100 and 50 pg.; the calculated regression line showed zero passage and possessed a correlation coefficient >0.998. Such a separation effectiveness and detection exactitude has hitherto not been possible.

Suitable silica gel particles useful in accordance with the present invention are in general all silica gels useful in conventional TLC which meet the physical requirements set forth above.

Compositions consisting of a silica gel with a particle size of between 3 and 8 $\mu$m and a weight related specific surface area of between 0.5 and 0.7 $m^2/g$. together with a binding agent and an indicator have hitherto not been used in chromatography.

These novel silica gel compositions which can be used for the production of the separating material for thin layer chromatography according to the invention consist in general of 85 to 99% of a silica gel of which at least 80% are 3 to 8 $\mu$m in diameter and possess a weight related specific surface area of between 0.5 and 0.7 $m^2/g$., 0.1 to about 10 weight % of a binding agent, usually employed for silica gel layers in thin layer chromatography, and 0.5 to 5 weight % of an indicator, also commonly used in thin layer chromatography sorption material. Preferred compositions consist of about 95 to 98% of a silica gel as specific above, 1 to 3% of a binding agent and 1 to 3% of an indicator. More preferred is a composition consisting of about 96.5% of a silica gel as specified above, 2% of a binding agent and 1.5% of an indicator.

The preferred binding agents are sodium acrylate and sodium methacrylate or mixtures thereof.

The preferred indicator is manganese activated zinc silicate.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

Physical values reported in the following examples were obtained as follows:

Specific surface area: Determinated according to the BET-method. For a reference to this method see S.T. Brunauer, Ph. Emmett, E. Teller, J. Amer. Chem. Soc. 60, 309 (1938).

Pore volume: Determined according to the method described by N.E. Fisher and A.Y. Mottlau in Anal. Chem. 34, 714 (1962).

Pore diameter: Calculated according to the method of P.C. Carman in J. Phys. Chem. 57, 56 (1953).

Particle size: Determined according to the WASPS-method (Wide Angle Scanning Photo-Sedimentometer). For a reference to this method see T. Allen in Silicates Industriels 36, 173 – 185 (1971).

Weight related specific surface area: These values correspond to a theoretical outer surface of the particles which is calculated from the particle size analysis under the assumption that all particles are isometric and possess no inner surface.

The calculation is based on the formula: Weight related specific surface area $$[cm^2/g.] = \frac{60\,000}{\bar{d} \cdot \rho}$$

whereby $\bar{d}$ [cm] is the average diameter of the particles and $\rho$ [g/cm$^3$] is the density of the solid material the particles consist of.

Preferred ranges for each of the thus-determined physical properties of TLC separating materials in accordance with the present invention are:

Particle size: 3 – 8 $\mu$m
Specific Surface Area: 400 – 700 $m^2/g$
Pore Volume: 0.5 – 1.0 ml/g
Pore Diameter: 40 – 100 A

EXAMPLE 1

Into a 400 l. vessel containing 240 l. of desalinated water are gradually added, with intensive stirring, 100 kg. of a mixture of 97% silica gel, 2% fluorescent indicator (manganese-activated zinc silicate) and 1% binding agent (sodium polyacrylate).

The silica gel used has a specific surface area of 500 $m^2/g$., a pore volume of 0.75 ml./g. and an average pore width of 60 A. Particle analysis, measured according to the WASPS method (Wide Angle Scanning Photo-Sedimentometer) in 0.034 vol.% aqueous solution at 24° C. (density of the silica gel = 2.24, factor 270) gives the following data:

smaller than 1.98 $\mu$m = 0.083 wt.%
1.98 – 2.00 $\mu$m = 0.005 wt.%
2.00 – 3.00 $\mu$m = 0.738 wt.%
3.00 – 5.00 $\mu$m = 38.670 wt.%
5.00 – 7.00 $\mu$m = 49.786 wt.%
7.00 – 9.26 $\mu$m = 10.718 wt.%

The following values are calculated therefrom:
$d_5$ = 3.8 $\mu$m
$d_{10}$ = 4.1 $\mu$m
$d_{50}$ = 5.2 $\mu$m
$d_{90}$ = 7.1 $\mu$m
$d_{95}$ = 7.9 $\mu$m $d$ is hereby in each case the limiting value. Thus, $d_5$ signifies that only 5 wt.% of the particles are smaller than the given value; $d_{95}$ correspondingly signifies that only 5 wt.% of the particles are larger than the given value.

The weight related specific surface area is 0.52 $m^2/g$.

After complete homogenization of the mass and removal of entrapped air under reduced pressure, glass plates of the size 200 × 200 × 1.2 mm. are coated using a conventional coating device and subsequently dried in a drying canal for 10 minutes at 150° C. The dry layer thickness is 175 μm.

EXAMPLE 2

Into a 4 l. vessel containing 2.6 l. of desalinated water are gradually added, with intensive stirring, 1 kg. of a mixture of 96.5% silica gel, 2.0% fluorescent indicator (manganese-activated zinc silicate) and 1.5% binding agent (sodium polymethacrylate).

The silica gel used has a specific surface area of 400 m²/g., a pore volume of 1.0 ml./g. and an average pore width of 100 A. Particle analysis, measured analogously to Example 1 in 0.031 vol.% aqueous solution at 24° C., given the following data:

smaller than 2.21 μm = 0.495 wt.%
2.21 – 3.00 μm = 2.065 wt.%
3.00 – 5.00 μm = 64.958 wt.%
5.00 – 7.00 μm = 21.504 wt.%
7.00 – 10.00 μm = 6.957 wt.%
10.00 – 11.95 μm = 4.020 wt.%

The following values are calculated therefrom:
$d_5 = 3.2$ μm
$d_{10} = 3.5$ μm
$d_{50} = 4.5$ μm
$d_{90} = 7.3$ μm
$d_{95} = 9.6$ μm The weight related specific surface area is 0.60 m²/g.

After complete homogenization of the mass, glass plates are coated and dried analogously to Example 1 to form a dry layer thickness of 225 μm.

EXAMPLE 3

Into a 40 l. vessel containing 23 l. of desalinated water are gradually added, with intensive stirring, 10 kg. of a mixture of 96% silica gel, 2% fluorescent indicator (manganese-activated zinc silicate) and 2% binding agent (sodium polyacrylate + sodium polymethacrylate 1:1).

The silica gel used has a specific surface area of 650 m²/g., a pore volume of 0.65 ml./g. and an average pore width of 40 A. Particle analysis, measured according to the WASPS method analogously to Example 1 in 0.038 vol.% aqueous solution at 24° C., gives the following data:

smaller than 2.66 μm = 0.512 wt.%
2.66 – 3.00 μm = 3,486 wt.%
3.00 – 5.00 μm = 70.905 wt.%
5.00 – 7.00 μm = 21.601 wt.%
7.00 – 10.00 μm = 2.689 wt.%
10.00 – 11.29 μm = 0.806 wt.%

The following values are calculated therefrom:
$d_5 = 3.1$ μm
$d_{10} = 3.4$ μm
$d_{50} = 4.4$ μm
$d_{90} = 6.0$ μm
$d_{95} = 6.3$ μm The weight related specific surface area is 0.62 m²/g.

After complete homogenization of the mass and removal of entrapped air under reduced pressure, aluminum foils in rolls 200 mm. wide and 100 μm thick and polyester films in rolls 200 mm. wide and 190 μm thick are coated on a conventional coating device. After drying, they are cut up into 200 × 200 mm. or 100 × 100 mm. squares. The dry layer thickness of the sorption agent layer is 125 μm.

EXAMPLE 4

Analogously to Example 1, 100 kg. of a mixture of 98% silica gel and 2% binding agent (sodium polyacrylate) are worked up to form a coatable suspension. The silica gel used has a specific surface area of 500 m²/g., a pore volume of 0.75 ml./g., an average pore width of 60 A. and is characterized by the following WASPS particle analysis:

smaller than 2.21 μm = 0.578 wt.%
2.21 – 3.00 μm = 4.789 wt.%
3.00 – 5.00 μm = 69.295 wt.%
5.00 – 7.00 μm = 18.795 wt.%
7.00 – 10.00 μm = 4.581 wt.%
10.00 – 11.95 μm = 1.961 wt.%

The following values are calculated therefrom:
$d_5 = 3.0$ μm
$d_{10} = 3.2$ μm
$d_{50} = 4.3$ μm
$d_{90} = 6.1$ μm
$d_{95} = 7.5$ μm The weight related specific surface area is 0.64 m²/g.

The layer thickness of the sorption agent on dried glass plates produced analogously to Example 1 is 200 μm.

EXAMPLE 5

Thin layer chromatography glass plates produced according to Example 1, after activation by heating for 15 minutes at 120° C., were employed for TLC separation. The speed coefficients kappa were determined in the case of thin layer chromatography in a normal chamber with chamber saturation at 22° C., with the use of benzene as the elution agent. Having regard to the elution agent level in the chromatography chamber, markings were applied on the layer at distances of 10 to 100 mm. After positioning the plate in the chamber, the times in each case which the elution agent front requires for a particular running distance were determined. The speed coefficient kappa (κ) is calculated according to the formula:

$$\kappa = z_f^2/t$$

whereby $z_f$ = running distance of the elution agent in mm., i.e., the distance between the level of dipping in and elution agent front; and $t$ = running time of the elution agent in sec.

The speed coefficient κ is dependent upon the elution agent used, the properties of the layer, the running height, the type of chamber and the temperature. The higher the κ value, the shorter is the running time in the case of a constant running height. The kappa values obtaned are shown in the following table.

Table 1

| $z_f$ mm. | t sec. | kappa mm²/sec. |
| --- | --- | --- |
| 10 | 26 | 3.8 |
| 20 | 96 | 4.2 |
| 30 | 200 | 4.5 |
| 40 | 324 | 4.9 |
| 50 | 470 | 5.3 |
| 60 | 636 | 5.7 |
| 70 | 822 | 6.0 |
| 80 | 1026 | 6.2 |
| 90 | 1246 | 6.5 |
| 100 | 1480 | 6.8 |

The values show that, especially in the case of the smaller running heights which are usually sufficient because of the high number of theoretical plates provided by the new separating agent, the development of the chromatogram takes only a few minutes. While not wishing to be bound by any theory of the invention, it is believed that the increasing speed coefficient $\kappa$ with an increasing running height can be explained, in the case of the use of a normal chamber with chamber saturation, by an increasing partial saturation of the pores via the vapor phase with the chromatography time.

EXAMPLE 6

This Example compares the separating material according to the present invention with the most effective hitherto known thin layer plate. For this purpose, a silica gel plate produced according to Example 1 was compared with a commercially available TLC finished plate (TLC finished plate silica gel 60 F 254, manufacturer E. Merck, Darmstadt) with regard to the height H of a theoretical plate. The H value is a measure of the separation effectiveness and corresponds to the so-called base height. The smaller the H value, the more concentrated is the chromatographic substance contained in the sorbent, the narrower are the peaks and the better is the separation (resolution) of neighboring substances. For better comparison, the H value is referred to an average hRf value of 50; in each case, the average values are given.

In the case of this comparative experiment, thin layer chromatographic separations were carried out in a lipophilic solvent system (benzene) in normal chambers with chamber saturation after previous activation of the layers by heating for 15 minutes at 120° C. At a distance of 15 mm. from the lower edge, 0.1 μl. of 0.1 wt.% in benzene solutions of the known dyestuffs Ceres violet BRN, Ceres green BB and Solvent Blue 35 were applied, with microcapillaries in multiple determinations. After positioning a TLC finished plate and a finished plate according to the invention (both 200 × 200 mm.) in the vessel (elution agent height 10 mm.), in separate experiments the developments were carried out with running heights of the elution agent of 20 mm. to 60 mm. The evaluations took place on a Zeiss Chromatogram spectrophotometer with a process calculator. The following average values were thereby obtained:

Table II

| running height of the elution agent in mm. | known TLC finished plate H value μm | TLC finished plate according to the invention H value μm |
|---|---|---|
| 20 | 66 | 24 |
| 30 | 46 | 19 |
| 40 | 36 | 18 |
| 50 | 32 | 17 |
| 60 | 32 | 18 |

The table clearly shows that the separating material according to the invention is substantially superior to the best known one in efficiency.

For illustration of the statements regarding the effective strength of the separating materials according to the invention, the relationship of the separation stage numbers were additionally determined.

Assumming a maximum hRf value of 80, from the above determined values there are obtained the relationships stated in Table III. It will be apparent from these data that the separation effectiveness of the finished plate according to the present invention is, on average, higher by a factor of 2 than that of the known comparison plate, the separation effectiveness of which is also already extraordinarily good.

Table III

| running stretch $z_f$ mm. | number of theoretical plates | | relationship of the numbers of theoretical plates (A:B) |
|---|---|---|---|
| | known TLC finished plate (A) | TLC finished plate according to the invention (B) | |
| 20 | 240 | 665 | 1:2.8 |
| 30 | 520 | 1265 | 1:2.4 |
| 40 | 890 | 1780 | 1:2.0 |
| 50 | 1250 | 2355 | 1:1.9 |
| 60 | 1500 | 2665 | 1:1.8 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a separating material for thin layer chromatography comprising a flat inert substrate having superimposed thereon a 100–300 μm thick layer of a sorption agent, wherein the improvement comprises said sorption agent consisting essentially of silica gel particles of which at least 80% are 3 to 8 μm in diameter, and not more than about 10% of said silica gel being either below 3 μm or about 8 μm, and the weight related specific surface area of said silica gel particles is 0.5–0.7 m²/g.

2. A separating material according to claim 1, wherein at least 85% of said particles are of said diameter.

3. A separating material according to claim 2, wherein at least 90% of said particles are of said diameter.

4. A separating material according to claim 1, wherein said inert substrate is selected from the group consisting of glass, aluminum foil and polyester films.

5. In a process for the separation of materials by thin layer chromatography by applying a sample to a separating material coated onto an inert substrate and developing the applied sample with a solvent, the improvement which comprises using as said separating material the separating material of claim 1.

6. In a process for the separation of materials by thin layer chromatography by applying a sample to a separating material coated onto an inert substrate and developing the applied sample with a solvent, the improvement which comprises using as said separating material the separating material of claim 2.

7. In a process for the separation of materials by thin layer chromatography by applying a sample to a separating material coated onto an inert substrate and developing the applied sample with a solvent, the improvement which comprises using as said separating material the separating material of claim 3.

8. In a process for the separation of materials by thin layer chromatography by applying a sample to a separating material coated onto an inert substrate and developing the applied sample with a solvent, the improvement which comprises using as said separating material the separating material of claim 4.

9. A separating material according to claim 1, wherein the silica gel particles have a specific surface area of 400 – 700 m²/g, a pore volume of 0.5 – 0.1 ml/g and a pore diameter of 40 – 100 A.

10. In a separating material for thin layer chromatography comprising a flat inert substrate having superimposed thereon a 100–300 μm thick layer of a sorption agent, wherein the improvement comprises said sorption agent being a silica gel composition consisting essentially of 85 to 99% of a silica gel of which at least 80% are 3 to 8 μm in diameter with a weight related specific surface area of between 0.5 to 0.7 m²/g., 0.1 to about 10 weight % of a binding agent and 0.5 to 5 weight % of an indicator.

11. A separating material for thin layer chromatography according to claim 10, wherein the amount of silica gel is about 96.5%, the amount of binding agent is about 2% and the amount of indicator is about 1.5%.

12. A separating material for thin layer chromatography according to claim 11, wherein the binding agent is sodium acrylate or sodium methacrylate or a mixture thereof and the indicator is manganese activated zinc silicate.

* * * * *